United States Patent
Brinker

(10) Patent No.: US 9,492,102 B2
(45) Date of Patent: Nov. 15, 2016

(54) OPTIMIZATION OF SPECIFIC ABSORPTION RATE PERFORMANCE

(71) Applicant: Gerhard Brinker, Erlangen (DE)

(72) Inventor: Gerhard Brinker, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 76 days.

(21) Appl. No.: 14/299,632

(22) Filed: Jun. 9, 2014

(65) Prior Publication Data

US 2014/0378823 A1   Dec. 25, 2014

(30) Foreign Application Priority Data

Jun. 21, 2013   (DE) .................. 10 2013 211 838

(51) Int. Cl.
| | | |
|---|---|---|
| A61B 5/055 | (2006.01) | |
| A61B 5/00 | (2006.01) | |
| G01R 33/28 | (2006.01) | |
| G01R 33/32 | (2006.01) | |
| G01R 33/563 | (2006.01) | |

(52) U.S. Cl.
CPC ............ *A61B 5/0555* (2013.01); *A61B 5/704* (2013.01); *G01R 33/288* (2013.01); *G01R 33/32* (2013.01); *A61B 5/055* (2013.01); *G01R 33/56383* (2013.01)

(58) Field of Classification Search
CPC .... A61B 5/055; A61B 5/0555; A61B 5/704; G01R 33/288; G01R 33/32; G01R 33/56383
See application file for complete search history.

(56) References Cited

U.S. PATENT DOCUMENTS 7,282,914 B2   10/2007   Morich et al.
2005/0127914 A1   6/2005   Eberler et al.

FOREIGN PATENT DOCUMENTS

DE   10314215   11/2006

OTHER PUBLICATIONS

German Search Report dated Feb. 17, 2014 for corresponding DE 102013211838.4.
Blumhagen, Jan O., et al., "MR-Based Field-of-View Extension in MR/PET: B0 Homogenization Using Gradient Enhancement (HUGE)," Magnetic Resonance in Medicine; vol. 70; pp. 1047-1057 (2013).

*Primary Examiner* — Mark Remaly
(74) *Attorney, Agent, or Firm* — Lempia Summerfield Katz LLC

(57) ABSTRACT

The embodiments relate to devices and methods for MRT imaging with a MRT, where a patient table having the scan subject is moved in at least one direction along at least one displacement path, determination of a quantity representing the SAR effect on the scan subject being carried out at a plurality of positions along the displacement path, a suitable position of the patient table, lying on a displacement path, being determined, at which the MRT imaging of the scan subject imaging region, to be scanned, of the scan subject is subsequently intended to be carried out.

19 Claims, 4 Drawing Sheets

OPTIMIZATION OF SPECIFIC ABSORPTION RATE PERFORMANCE

CROSS-REFERENCE TO RELATED APPLICATIONS

This application claims the benefit of DE 10 2013 211 838.4, filed on Jun. 21, 2013, which is hereby incorporated by reference in its entirety.

TECHNICAL FIELD

The embodiments relate to methods and devices for the optimization of magnetic resonance tomograph (MRT) imaging and/or specific absorption rate (SAR) performance with a MRT.

BACKGROUND

Magnetic resonance tomographs (MRTs) for scanning objects or patients by magnetic resonance tomography are known, for example, from DE 103 14 215 B4.

SUMMARY

It is an object of the present embodiments to optimize the SAR performance of a MRT.

The scope of the present invention is defined solely by the appended claims and is not affected to any degree by the statements within this summary. The present embodiments may obviate one or more of the drawbacks or limitations in the related art.

DETAILED DESCRIPTION

Figure 4:
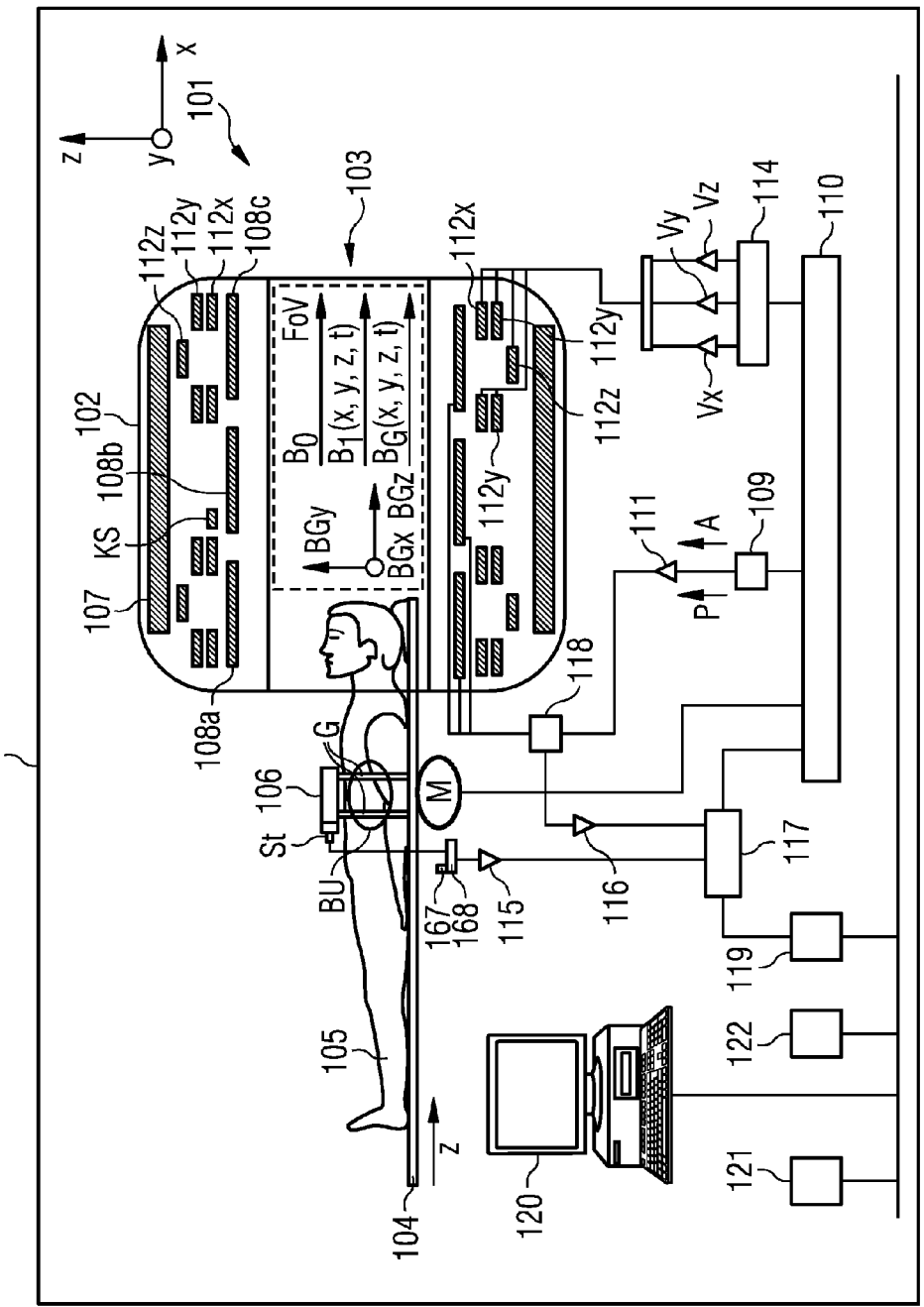
FIG. 4 schematically depicts an embodiment of a MRT system.

FIG. 4 depicts an imaging magnetic resonance tomograph MRT 101 (located in a shielded space or Faraday cage F) having a body coil 102 with a space 103, which is tubular in this case, in which a patient table 104 with a body or a scan subject 105 (e.g., a patient), with or without a local coil arrangement 106, may be displaced in the direction of the arrow z in order to generate recordings of the scan subject 105 by an imaging process. In this case, a local coil arrangement 106 is arranged on the patient, with which coil arrangement, in a local region (also referred to as a field of view or FoV) of the MRT, recordings of a (scan subject imaging) region BU of the body 105 may be generated in the FoV (generated by MRT imaging). Signals of the local coil arrangement 106 may be evaluated (for example, converted into images, stored, or displayed) by an evaluation device (168, 115, 117, 119, 120, 121, etc.) of the MRT 101, which may be connected to the local coil arrangement 106, for example, by coaxial cable or by radio 167, etc.

In order to scan a body 105 (a scan subject or a patient) with a magnetic resonance tomograph MRT 101 by magnetic resonance imaging, the body 105 is exposed to various magnetic fields matched with one another as accurately as possible in terms of their temporal and spatial characteristics. A strong magnet (often a cryomagnet 107) in a measurement space, here with a tunnel-shaped opening 103, generates a strong static main magnetic field $B_0$, which is, for example, from 0.2 tesla (T) to 3 tesla (T) or more. A body 105 to be scanned is displaced, while lying on a patient table 104, into an approximately homogeneous region of the main magnetic field $B_0$ in the observation region FoV (field of view). Excitation of the nuclear spins of atomic nuclei of the body 105 is carried out by radiofrequency magnetic excitation pulses $B_1(x, y, z, t)$, which are applied by a radiofrequency antenna represented here in a very simplified way as a (e.g., multipart=108a, 108b, 108c) body coil 108 (and/or optionally a local coil arrangement). Radiofrequency excitation pulses are generated, for example, by a pulse generation unit 109, which is controlled by a pulse sequence control unit 110. After amplification by a radiofrequency amplifier 111, the pulses are delivered to the radiofrequency antenna 108. The radiofrequency system depicted here is merely indicated schematically. Often, more than one pulse generation unit 109, more than one radiofrequency amplifier 111 and a plurality of radiofrequency antennas 108a, 108b, 108c are used in a magnetic resonance tomograph 101.

The magnetic resonance tomograph 101 furthermore has gradient coils 112x, 112y, 112z, with which gradient magnetic fields $B_G(x, y, z, t)$ are applied during a measurement for selective slice excitation and for position encoding of the measurement signal. The gradient coils 112x, 112y, 112z are controlled by a gradient coil control unit 114 (and optionally by amplifiers Vx, Vy, Vz) that, like the pulse generation unit 109, is connected to the pulse sequence control unit 110.

Signals emitted by the excited nuclear spins (of the atomic nuclei in the scan subject) are received by the body coil 108 and/or at least one local coil arrangement 106, amplified by associated radiofrequency preamplifiers 116, and further processed and digitized by a receiver unit 117. The recorded measurement data are digitized and stored as complex numerical values in a k-space matrix. From the k-space matrix populated with values, an associated MR image may be reconstructed by a multidimensional Fourier transform.

For a coil that may be operated in both transmit and receive mode, for example the body coil 108 or a local coil 106, the appropriate signal forwarding is regulated by an upstream transmit/receive switch 118. From the measurement data, an image processing unit 119 generates an image that is represented to a user on a control console 120 and/or stored in a storage unit 121. A central computer unit 122 controls the individual system components.

In MR tomography, images with a high signal/noise ratio (SNR) may be acquired with so-called local coil arrangements. These are antenna systems that are placed in direct proximity on (anterior), under (posterior), on the body 105, or in the body 105. During a MR measurement, the excited nuclei induce a voltage in the individual antennas of the local coil, which voltage is amplified with a low-noise preamplifier (LNA, preamp) and finally forwarded to the reception electronics. In order to improve the signal-to-noise ratio even in the case of high-resolution images, so-called high-field systems are used (1.5 T-12 T or more). If more individual antennas may be connected to a MR reception system than there are receivers, a switching matrix (also referred to as a RCCS) is, for example, installed between the reception antennas and the receivers. This routes the currently active reception channels (e.g., those that lie in the field of view of the magnet) to the receivers provided. In this way, it is possible to connect more coil elements than there are receivers, since in the case of whole body coverage, it is only necessary to read the coils that lie in the FoV (Field of View) or in the homogeneity volume of the magnet.

A local coil arrangement 106 may refer, for example, to an antenna system that may, for example, include one antenna element or, as an array coil, a plurality of antenna elements (e.g., coil elements). These individual antenna elements are configured, for example, as loop antennas, butterflies, flex coils, or saddle coils. A local coil arrangement includes, for example, coil elements, a preamplifier, further electronics (sheath wave traps, etc.), a housing, supports, and, for example, a cable with a jack, by which the cable is connected to the MRT system. A receiver 168 fitted on the system side filters and digitizes a signal received from a local coil 106, for example, by radio, etc., and transfers the data to a digital signal processing device. The signal processing device may derive an image or a spectrum from the data obtained by a measurement and provide the image or spectrum to the user, for example, for subsequent diagnosis by him, and/or storage.

FIGS. 1 to 4 illustrate non-limiting examples of methods and devices for optimization of the SAR performance by determining an optimum position $z_{opt}$, $y_{opt}$, $x_{opt}$ of the patient relative to, e.g., a (RF) transmission coil and/or e.g. relative to a FoV (e.g., the midpoint $M_{FoV}$).

During a MRT scan, the position BU to be scanned in the body of the scan subject (for example, a patient) may be positioned, for example, as centrally as possible in the magnet, since the homogeneity of the base magnetic field $B_0$ is maximum there. To this end, with a patient table 104, a patient 105 lying on the patient table 104 is displaced into the magnet (e.g., into the MRT bore in the magnet) 103 until the patient's region BU to be scanned lies, for example, under a position marking device (e.g., light field indicator, laser marker).

This position is registered, and the patient is subsequently moved from the marked position exactly to the center (for example, into the FoV and/or its midpoint or center $M_{FoV}$). The patient table 104 in this case moves along the longitudinal axis z of the (base-field) magnet of the MRT. This will subsequently be referred to as the z axis, and the respective positions ($Pos_1$, $Pos_2$, $Pos_3$, $Pos_4$, $Pos_5$) along this axis as "z positions". The position at the center $M_{FoV}$ of the FoV will be assigned, for example, to the position z=0 (in FIG. 1). The adjustments are carried out at the position z=0, and measurement programs with settings based on the adjustment results are loaded and started.

With respect to performance in the sense of how fast scans may be carried out with optimum image quality, determination of the drive amplitude of the RF amplifier provided for the desired flip angle is of importance. This adjustment procedure will be referenced or denoted below by AdjTra. An at least internal measurement experience depicts that the AdjTra result very much depends on the current position of the patient relative to the transmission coil. The sensitivity and the extent of the variation of the AdjTra result to a change in the position increases with the field strength of the base magnetic field. The consequence is that with an unfavorable position the intended measurement program may not be started, since the RF exposure to the patient associated therewith would exceed the permissible SAR limit values (for example, SAR as power per kg indicated in FIG. 2 as a rectangle) in the course of the measurement program.

If a measurement program may not be started because the SAR limit values would be exceeded, suitable parameters of the measurement program are changed in such a way as to comply with the SAR limits in the course of the measurement. Often, according to an at least internally known solution, the number of slice images that are acquired simultaneously in the course of the measurement program is reduced, or the measurement time is extended so that some of the slice images are acquired with a time offset, or the duty cycle is reduced by simply increasing the repetition time of repeating RF pulse sequences. Another at least internally known strategy is to reduce the flip angle of power-intensive RF pulses. Further at least internally known possibilities exist, for example using different pulse shapes.

The volume usable for the clinical imaging (FoV) at the center of the magnet may have a diameter of 40 cm to 50 cm. The position marked before the final introduction of the patient thus does not necessarily have to lie exactly at the center in order to image the volume by MR. An at least internal measurement experience depicts that displacement (e.g., moving) of the patient table 104 by only a few centimeters leads to a relatively large variation in the AdjTra result, and therefore the SAR value associated with the measurement program. With a patient 105 positioned in the region of the torso, at 3 T with displacement of the patient table 104 by only 2.5 cm, increases (in the SAR) by up to 100%, or reductions by up to 50% may be established (expressed in terms of power). In order to optimize the performance, it is therefore advantageous to determine the AdjTra results at a sensible distance (e.g., 2, 5, or 10 centimeters) in both directions along the z axis with a sufficient spatial resolution (e.g., one millimeter or a few millimeters) and to displace the patient table 104 into the position with the minimum AdjTra result (more precisely, for example, the "SAR/BF" ratio), so that the measurement programs may be carried out with optimum performance. Since the duration of an AdjTra procedure may lay in the sub-second range (less than one second), the time taken is tolerable in view of an overall scan time of, for example, 25 minutes. The process may also be optimized by determining the AdjTra values (for example, SAR values, P, A, etc. as a function of position) continuously during the inward displacement. In addition, with the aid of the registered scan type, a decision may be made as to how far the initial determination of the adjustment results may take place beyond the marked z position, since it is to be expected that these regions will also be occupied in the course of the scan. The respective AdjTra results may be stored as a function of the z position, and may be read out again and used as needed.

In the individual measurement protocols, it is possible to define whether the measurement may be carried out with a position offset (for example tolerated distance T/2 from the center $M_{FoV}$) and if so how great the maximum offset may be (optionally direction-dependently for +−x, +−y, +−z). With the aid of the AdjTra results obtained (P, A, etc.), it is possible to select the result that still lies in the allowed range T and leads to a minimum SAR. This position offset (for example, distance PO of a position $Pos_2$ from the center $M_{FoV}$ of the FoV) is naturally to be taken into account sequence-internally in the generation of the MR images (slice offset, etc.).

One embodiment may include the use of (at least internally found) measurement experience that the drive amplitude A, and therefore also the RF transmit power P, for the RF amplifier. The transmit power P is provided in order to generate a desired flip angle for a given RF pulse shape, and therefore also the SAR value (influenced as a function of power P and/or amplitude A by dependency of the extent of the (SAR and/or RF) influence of RF pulses (of RF coils) on the scan subject). Because of interaction of the complexly constructed RF transmission antennas with the very inhomogeneous body of the patient lying in the absolute near field, the drive amplitude A often has a very steep gradient with the change in the position in the direction of the z axis. This measurement experience, in combination with the fact (result) that the body region BU marked by the positioning unit need not lie exactly at the center $M_{FoV}$ of the magnet, makes it possible to select the AdjTra result most favorable in respect of performance, to displace the patient table 104 accordingly, and to carry out the measurement there with necessary adaptation of the measurement parameters (position offset PO, P, A, etc.). A restriction for the AdjTra result ($Pos_2$) to be selected may be that the result may have been determined in the defined tolerance range T with respect to the (z and/or y and/or x) position.

Figure 1:
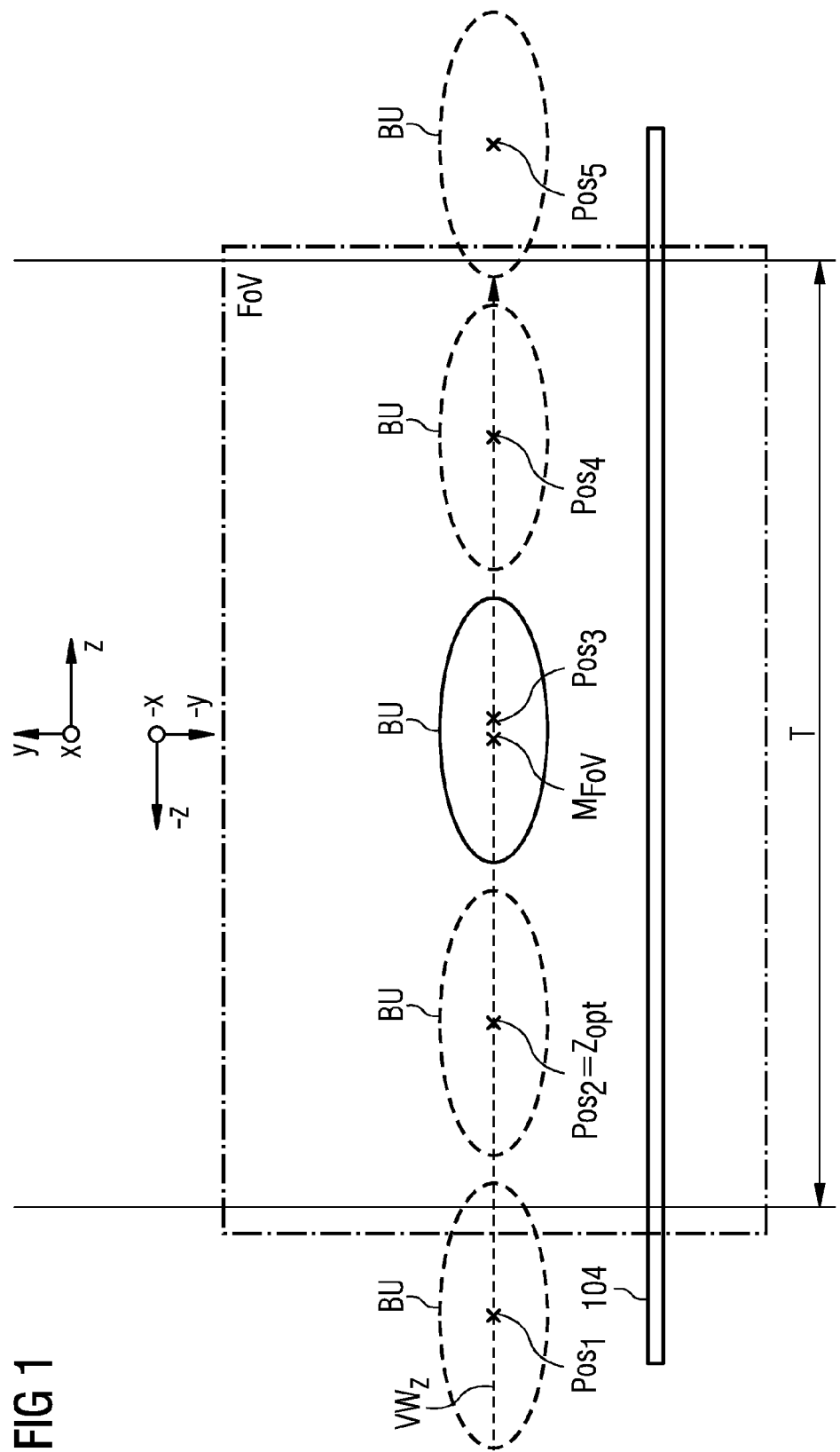
FIG. 1 depicts an embodiment of a field of view of a MRT, in which a patient table with a scan subject is moved in a direction z so as to determine a position of the patient table that is particularly suitable with respect to SAR for subsequent MRT imaging.

As a non-limiting example, FIG. 1 schematically depicts as a detailed representation (as a partial excerpt of FIG. 4) a patient table 104 with a region BU to be scanned of a scan subject 105. The subject 105 is moved in a direction z along a displacement path $VW_z$. A determination of a quantity (such as the power P and/or the amplitude A for an amplifier and/or an AdjTra value and/or measured SAR values, etc.) representing the (SAR and/or RF) influence on the scan subject 105 respectively is carried out at a plurality of positions ($Pos_1$, $Pos_2$, $Pos_3$, $Pos_4$, $Pos_5$) along the displacement path $VW_z$. Additionally, a position $z_{opt}$ (at position $Pos_2$) of the patient table 104 lying on a displacement path $VW_z$, which is suitable (for example, because of a minimum value P and/or A provided for the formation of a pulse shape and/or a flip angle, etc.), is determined, at which ($Pos_4$, $z_{opt}$) the MRT imaging (that is to say for example generation of at least one image of the region BU by at least one MRT measurement sequence, etc.) of the imaging scan subject imaging region BU, to be imaged, of the scan object 105 is subsequently intended to be carried out.

Figure 2:
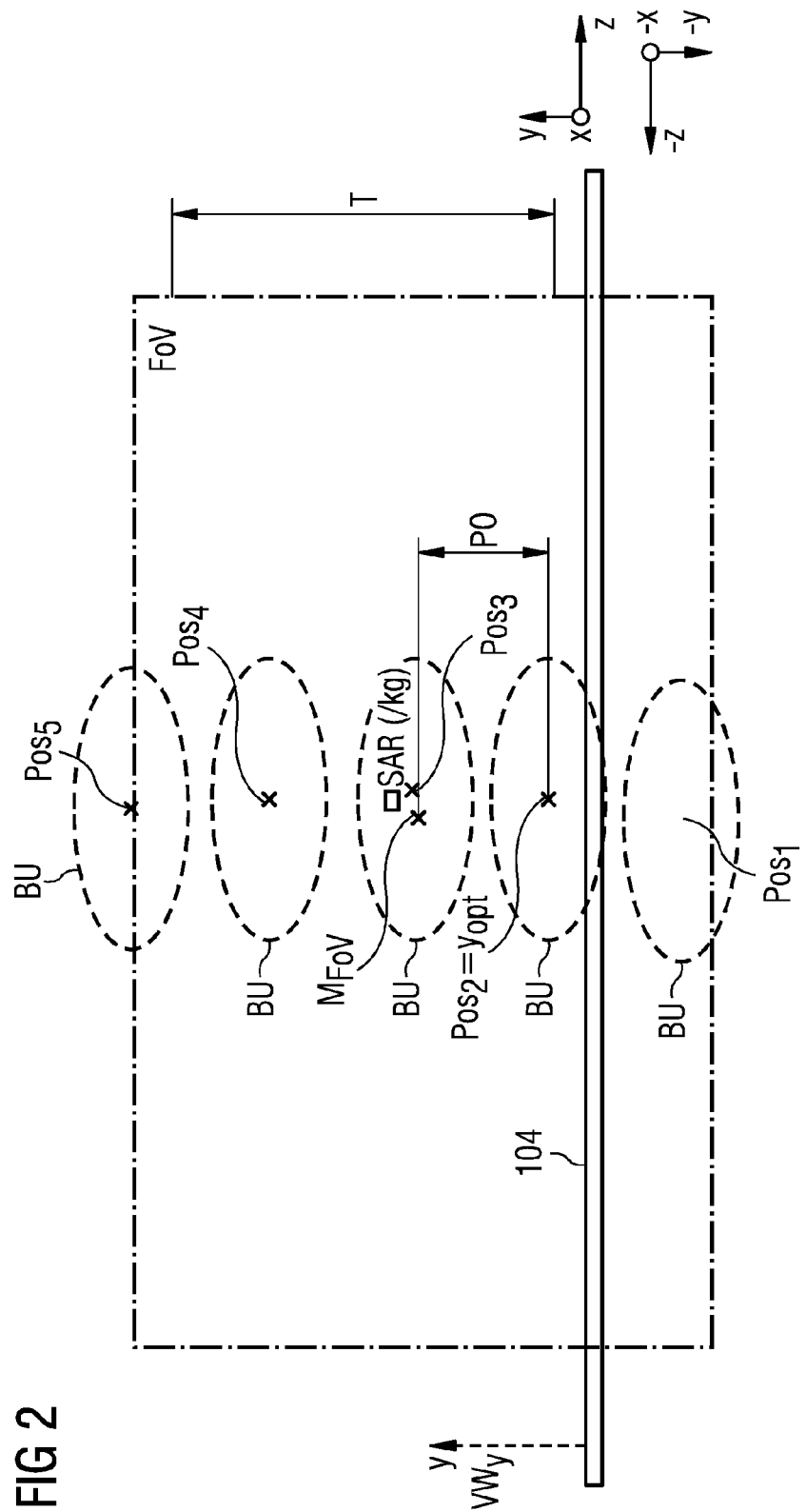
FIG. 2 depicts an embodiment a field of view of a MRT, in which a patient table with a scan subject is moved in a direction y so as to determine a position of the patient table that is suitable with respect to SAR for subsequent MRT imaging.

FIG. 2 depicts, as another non-limiting example (which may be combined with the example in FIG. 1 and/or a displacement in a further direction x), having a patient table 104 that has a scan subject 105. The subject is moved in a direction y (+y and/or −y) along a displacement path $VW_y$. A determination of a (SAR) quantity (such as the power P and/or the amplitude A for an amplifier and/or an AdjTra value and/or measured SAR values, etc.) representing the (SAR and/or RF) influence on the scan subject 105 respectively is carried out at a plurality of positions ($Pos_1$, $Pos_2$, $Pos_3$, $Pos_4$, $Pos_5$) along the displacement path $VW_y$. A position $y_{opt}$ (at position $Pos_2$) of the patient table 104 lying on a displacement path $VW_y$, which is suitable (for example because of a minimum value P and/or A provided for the formation of a pulse shape and/or a flip angle, etc.), is determined, at which ($Pos_4$, $y_{opt}$) the MRT imaging (that is to say generation of at least one image by a MRT measurement sequence, etc.) of the imaging scan subject imaging region BU, to be imaged, of the scan object 105 is subsequently intended to be carried out.

A quantity representing the RF influence on the scan subject 105 may, for example, be a quantity that influences how much RF energy and/or power (in total or by weight, etc.) is applied to the scan subject 105, BU (in total or in a period of time or at a point in time), for example, the power P or the amplitude with which a RF amplifier (at least one or the sum of the RF amplifiers) is driven, etc. A quantity representing the RF influence on the scan subject 105 may also, for example, be a quantity that influences how much RF energy and/or power (in total or by weight, etc.) was absorbed by the scan subject 105, BU (in total or in a period of time or at a point in time), for example, its calculated or measured heating.

Figure 3:
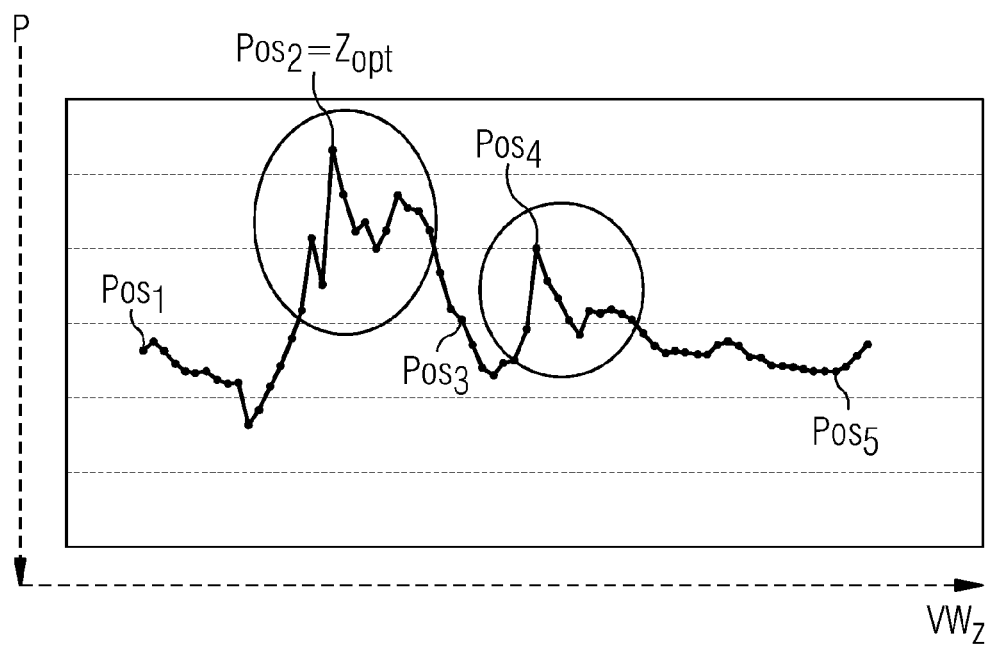
FIG. 3 depicts a measured quantity, representing the SAR effect on the scan subject, in the form of, for example, the radio frequency (RF) amplifier drive amplitude A and/or RF amplifier power P provided for forming a desired pulse shape and/or a desired flip angle, etc.

FIG. 3 depicts a value P that is determined at a plurality of positions $Pos_1$, $Pos_2$, $Pos_3$, $Pos_4$, $Pos_5$ along the displacement path ($VW_y$, $VW_z$ and/or in the x direction), for example, the RF amplifier drive amplitude A and/or power P for the driving of a RF amplifier 11 by a controller 110, which, for example (A; P), is provided and/or used in order to form a RF pulse shape and/or a flip angle, etc.

The instructions for implementing processes or methods described herein may be provided on non-transitory computer-readable storage media or memories, such as a cache, buffer, RAM, FLASH, removable media, hard drive, or other computer readable storage media. A processor performs or executes the instructions to train and/or apply a trained model for controlling a system. Computer readable storage media include various types of volatile and non-volatile storage media. The functions, acts, or tasks illustrated in the figures or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Likewise, processing strategies may include multiprocessing, multitasking, parallel processing and the like.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for magnetic resonance tomograph imaging with a magnetic resonance tomograph, the method comprising:
    moving, using a controller, a patient table having a scan subject in at least one direction along at least one displacement path;
    determining a quantity representing a radio frequency (RF) influence on the scan subject at a plurality of positions along the at least one displacement path; and
    determining, as a function of the quantity, a first position of the patient table lying on the at least one displacement path at which the magnetic resonance tomograph imaging of an imaging region is to be scanned.

2. The method as claimed in claim 1, wherein the patient table is moved along only one displacement path or in only one direction in order to determine the first position.

3. The method as claimed in claim 1, wherein the patient table is moved along more than one displacement path or in more than one direction in order to determine at least one first position.

4. The method as claimed in claim 1, wherein the patient table is moved is a direction in which the scan subject is introduced into a field of view of the magnetic resonance tomograph.

5. The method as claimed in claim 1, wherein one or two of the directions in which the patient table is moved is or are orthogonal to a direction in which the scan subject is introduced into a field of view of the magnetic resonance tomograph.

6. The method as claimed in claim 1, wherein the displacement path is less than twenty centimeters long.

7. The method as claimed in claim 1, wherein the first position of the patient table is relative to a midpoint of a field of view of the magnetic resonance tomograph or relative to at least one RF transmission coil of the magnetic resonance tomograph.

8. The method as claimed in claim 1, wherein the first position lies outside a midpoint of a field of view of the magnetic resonance tomograph.

9. The method as claimed in claim 1, wherein the first position lies in such a way that a part of the imaging region lies outside a field of view of the magnetic resonance tomograph.

10. The method as claimed in claim 1, wherein the first position is determined only from positions of the plurality of positions that lie within a predetermined or stored spatial tolerance range with respect to the first position, wherein the stored spatial tolerance range is a maximum distance of the first position from a midpoint of a field of view.

11. The method as claimed in claim 10, wherein the stored spatial tolerance range is less than 10 centimeters.

12. The method as claimed in claim 1, wherein by a tolerance range respectively stored in the magnetic resonance tomograph for one or more measurement protocols, a maximum distance as a position offset of a suitable position from a midpoint of a field of view is taken into account during the determination of the first position from the plurality of positions.

13. The method as claimed in claim 1, wherein the first position of the patient table is a position at which there is a local or global minimum of the quantity representing the RF influence on the scan subject.

14. The method as claimed in claim 1, wherein the quantity representing the RF influence on the scan subject is a measured specific absorption rate (SAR) or a SAR calculated with a model.

15. The method as claimed in claim 1, wherein the first position of the patient table is determined before the magnetic resonance tomograph imaging with the magnetic resonance tomograph, at which a drive amplitude or power for a RF amplifier of the magnetic resonance tomograph, used for a desired flip angle, a desired RF pulse shape during the magnetic resonance tomograph imaging, or a SAR/BF ratio, is minimized.

16. The method as claimed in claim 1, wherein during the displacement of the patient table along a displacement path, a drive amplitude or power of a RF amplifier of the magnetic resonance tomograph, used for a desired flip angle during the magnetic resonance tomograph imaging or a SAR/BF ratio, is determined at the plurality of positions.

17. The method as claimed in claim 1, wherein in order to determine the quantity representing the RF influence on the scan subject, determined values are stored as a function of the position of the plurality of positions at which the determined values were determined.

18. The method as claimed in claim 1, further comprising generating a magnetic resonance tomograph image, wherein a position offset between the first position and a midpoint of a field of view of the magnetic resonance tomograph is taken into account when generating the magnetic resonance tomograph image.

19. A non-transitory computer-readable storage medium having stored therein a computer program for controlling a target system when executed by a computer, the storage medium comprising instructions for:
moving a patient table having a scan subject in at least one direction along at least one displacement path;
determining a quantity representing a radio frequency (RF) influence on the scan subject at a plurality of positions along the at least one displacement path; and
determining, as a function of the quantity, a first position of the patient table lying on the at least one displacement path at which a magnetic resonance tomograph imaging of an imaging region is to be scanned.

* * * * *